US 8,430,054 B1

(12) United States Patent
Hunter et al.

(10) Patent No.: US 8,430,054 B1
(45) Date of Patent: Apr. 30, 2013

(54) PORTABLE FINGERPRINT DEVELOPMENT SYSTEM

(75) Inventors: Jim Hunter, Olathe, KS (US); Mark S. Schmitz, Overland Park, KS (US); Mark Schultz, Altamont, KS (US)

(73) Assignee: Labconco Corporation, Kansas City, MO (US)

( * ) Notice: Subject to any disclaimer, the term of this patent is extended or adjusted under 35 U.S.C. 154(b) by 584 days.

(21) Appl. No.: 12/783,121

(22) Filed: May 19, 2010

(51) Int. Cl.
*C23C 16/00* (2006.01)
*C23C 16/458* (2006.01)

(52) U.S. Cl.
USPC .......... 118/31.5; 118/715; 118/728; 118/729; 118/731

(58) Field of Classification Search ............ 118/31.5, 118/715, 728, 729, 731
See application file for complete search history.

(56) References Cited

U.S. PATENT DOCUMENTS

| | | | | |
|---|---|---|---|---|
| 3,851,619 | A * | 12/1974 | Cofield et al. | 118/31.5 |
| 3,960,632 | A * | 6/1976 | Gaines et al. | 156/245 |
| 4,297,383 | A * | 10/1981 | Bourdon | 427/1 |
| 4,700,657 | A * | 10/1987 | Butland | 118/31.5 |
| 5,266,112 | A * | 11/1993 | Crosbie | 118/31.5 |
| 5,395,445 | A * | 3/1995 | Bohanan | 118/31.5 |
| 5,465,765 | A * | 11/1995 | Martindale | 141/65 |
| 6,423,946 | B1 * | 7/2002 | Berka et al. | 219/390 |
| 6,660,054 | B2 * | 12/2003 | Manna et al. | 55/385.2 |
| 7,487,739 | B1 * | 2/2009 | Weaver et al. | 118/31.5 |
| 8,272,343 | B1 * | 9/2012 | Weaver et al. | 118/31.5 |
| 2002/0124537 | A1 * | 9/2002 | Manna et al. | 55/385.2 |
| 2011/0033607 | A1 * | 2/2011 | Pitts et al. | 427/1 |

OTHER PUBLICATIONS

Sirchie Finger Print Laboratories, "Cyanovac I Laboratory Fuming Chamber Outfit", on sale more than one year prior to May 19, 2010, the effective filed of this application, downloaded from the internet on Oct. 29, 2010.
Collapsible Chambers, on sale more than one year prior to May 19, 2010, the effective filing date of this application.
CNA 1000 Chamber, on sale more than one year prior to May 19, 2010, the effective filing date of this application.
Insta-Fume Tent, on sale more than one year prior to May 19, 2010, the effective filing date of this application.
Coffee Cup Warmer, on sale more than one year prior to May 19, 2010, the effective filing date of this application.
Cyanowand glue fuming device, on sale more than one year prior to May 19, 2010, the effective filing date of this application.
Fuminator, on sale more than one year prior to May 19, 2010, the effective filing date of this application.
DeFumigator, on sale more than one year prior to May 19, 2010, the effective filing date of this application.

(Continued)

*Primary Examiner* — Jeffrie R Lund
(74) *Attorney, Agent, or Firm* — Stinson Morrison Hecker LLP (57) ABSTRACT

A portable fingerprint development system having a container and a base plate. The container includes a plurality of joined walls that present an opening and a rim surrounding the opening. The base plate has opposed first and second surfaces. The first surface mounts a heater that is operable to heat a fingerprint development material. The base plate is moveable between a transport position, in which the first surface is adjacent the container's rim and the heater is positioned within the container, and an operation position, in which the second surface is adjacent the container's rim to enclose an interior volume defined by the container's walls and the base plate. Preferably, an exhaust system is mounted on the first surface of the base plate for removing and/or filtering fumes within the container.

28 Claims, 9 Drawing Sheets

OTHER PUBLICATIONS

Misonix Cyanoacrylate Fuming Chamber, on sale more than one year prior to May 19, 2010, the effective filing date of this application.
Air Clean CyanoSafe, on sale more than one year prior to May 19, 2010, the effective filing date of this application.
Air Science SafeFume, on sale more than one year prior to May 19, 2010, the effective filing date of this application.
Hamilton Forensic Cabinets, on sale more than one year prior to May 19, 2010, the effective filing date of this application.

* cited by examiner

PORTABLE FINGERPRINT DEVELOPMENT SYSTEM

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

1. Field of the Invention

The present invention relates generally to latent fingerprint development, and more particularly, to a portable fingerprint development system.

2. Description of Related Art

Fingerprint development systems have been used for a number of years to develop latent fingerprints on crime scene evidence. One common method for developing latent fingerprints consists of vaporizing cyanoacrylate within an enclosure containing evidence whereby the cyanoacrylate forms a white polymer on the ridges of fingerprints on the evidence. While there are a number of large, stationary systems available to perform this process effectively in the lab, available portable systems that can be used by forensic investigators and police officers to develop latent fingerprints at a crime scene have limited functionality. Further, it is highly advantageous to develop prints at a crime scene to reduce the risk that the prints will be smeared or rubbed off when the evidence is handled and transported from the crime scene to the lab.

For example, most portable fingerprint development systems are made of collapsible "knock-down" chambers or tents that can be carried to the crime scene in a collapsed form and are then put together at the scene for use. While these systems are relatively easy to transport, they take time to put together at the scene and do not seal well or have any form of exhaust system for venting the cyanoacrylate fumes. In addition, some of these systems are disposable and therefore not suitable for long-term or multiple uses.

Most of the portable systems known to date also require a separate heating element to vaporize the cyanoacrylate. One method used with these systems for vaporizing cyanoacrylate consists of placing a heating element such as a coffee cup warmer within the chamber and positioning cyanoacrylate adjacent to the heating element. With this method it is difficult to control the amount of cyanoacrylate vapor filling the chamber in order to prevent overdeveloping the fingerprints. Further, it can be awkward to place such a warmer into the chamber and route the electrical cord out of the chamber. Another method for heating cyanoacrylate consists of using a fuming wand that burns butane to heat a solid cyanoacrylate cartridge placed on the tip of the wand. The wand's tip is placed adjacent to an opening in a collapsible chamber so that fumes emanating from the wand enter the chamber. While the wand is easier to control than a heating element positioned within the chamber, care must be taken to prevent injury or damage to the chamber or evidence positioned therein due to the heat of the ignited butane.

Thus, while conventional portable fingerprint development systems are generally effective to develop latent fingerprints, each has drawbacks limiting its functionality.

BRIEF SUMMARY OF THE INVENTION

The present invention is directed toward a portable fingerprint development system comprising an integrated heater for vaporizing fingerprint development material and, optionally, also including an integrated exhaust system for filtering and exhausting the vaporized material after completion of the fingerprint development process. The portable system comprises a container and a base plate which mounts to the container in a transport position and an operation position. The container is formed from a plurality of joined walls that define an interior accessible via an opening. The base plate has opposed first and second surfaces with a heater being mounted on the first surface. In the transport position, the first surface of the base plate is positioned facing or adjacent the container's opening and the heater is positioned within the container. In this transport position, the system is preferably relatively compact and lightweight such that it may be transported by a single person. In the operation position, the second surface of the base plate is positioned facing or adjacent the container's opening to substantially enclose the interior for purposes of developing latent fingerprints on evidence placed within the interior. In this operation position, the heater is operable to vaporize fingerprint development material within a compartment that is in fluid communication with the interior of the container. In this manner, the vaporized material flows into the interior of the container for developing latent fingerprints on the evidence that has been placed within the container.

In one embodiment, the fingerprint development system preferably comprises a heater compartment mounted on the first surface of the base plate adjacent the heater. The heater compartment preferably comprises at least one well for receiving a fingerprint development material such as cyanoacrylate. Most preferably, the heater compartment also comprises a second well for receiving water. The heater compartment is preferably in fluid communication with the interior of the container so that vaporized fingerprint development material within the heater compartment can flow into the container and develop latent fingerprints on an object within the container.

The system also preferably comprises an exhaust system that is mounted to the first surface of the base plate. The exhaust system preferably comprises a conduit that is in fluid communication with the interior of the container when the base plate is in its operation position for exhausting fumes from within the container. Preferably, there is at least one filter positioned within the conduit for filtering cyanoacrylate fumes passing through the conduit. Most preferably, the conduit contains a particulate filter for removing droplets of cyanoacrylate from the air passing through the conduit and activated carbon granules for filtering vaporous cyanoacrylate.

The system also preferably comprises a temperature controller for regulating the temperature of the heater. Most preferably, the controller comprises a user input device for receiving a desired heater temperature from an operator and a display for displaying both the desired heater temperature and the actual heater temperature.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be

DETAILED DESCRIPTION OF PREFERRED EMBODIMENT

Figure 1:
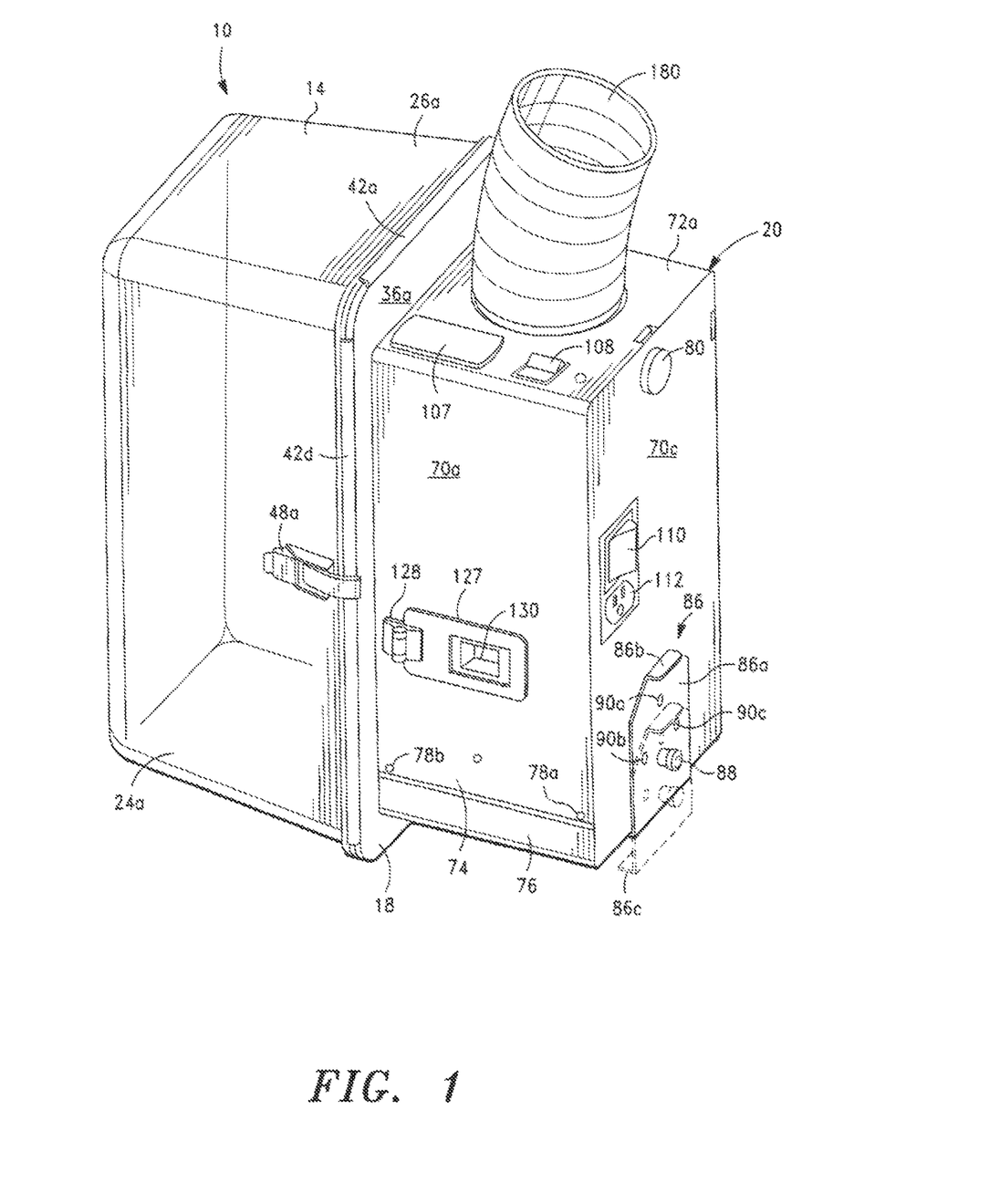
FIG. 1 is a perspective view of a portable fingerprint development system in accordance with the present invention.

Referring to FIG. 1, a portable fingerprint development system in accordance with a preferred embodiment of the present invention is shown generally as 10. The portable system 10 has an operation position that is shown in FIGS. 1-5 and 7-8 and a transport position that is shown in FIGS. 9-12. In its operation position, the system 10 is operable to develop latent fingerprints on objects or evidence, such as the handgun 12 shown in FIG. 2, suspended within a transparent container 14. In its transport position, the system 10 is relatively compact and may be easily transported to a crime scene or other desirable location by a single person. Preferably, the system 10 weighs between approximately 20 to 25 pounds. Preferably, when in the transport position shown in FIG. 10, the system 10 has a height of approximately 9 to 10 inches, a length of approximately 18 to 20 inches, and a width of approximately 10 to 12 inches. The system 10 includes container 14, a base plate 18 that is mounted to the container in the operation position and the transport position, and a housing 20 that is mounted to the base plate 18. The system 10 is additionally protected when in its transport position by cover 16 (FIG. 10).

Figure 7:
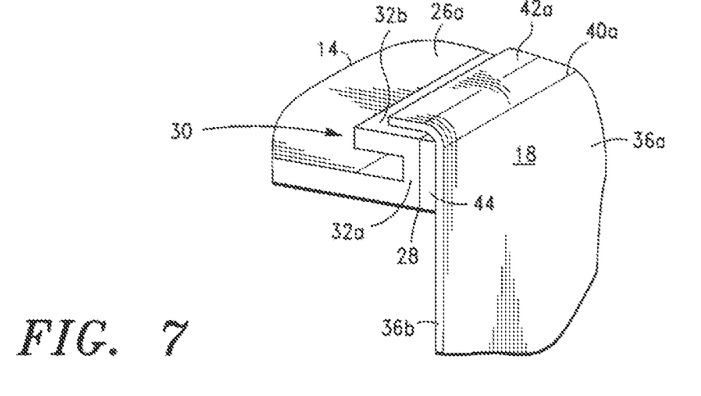
FIG. 7 is a close-up view of sealing edges of a base plate and container of the system of FIG. 1.

The container 14 has a rear wall 22 (FIG. 2) with front and back side walls 24a (FIGS. 1-3) and 24b (FIG. 4) and end walls 26a (FIGS. 1-3) and 26b (FIG. 5) integrally formed or joined with and extending outwardly from rear wall 22 to present an opening 28 positioned opposite rear wall 22. As shown in FIGS. 5 and 7, a continuous rim 30 is integrally formed or joined with sidewalls 24, 26 along the perimeter of opening 28. Referring to FIG. 7, rim 30 is generally C-shaped with a first leg 32a extending generally perpendicular and outward from side walls 24, 26 and a second leg 32b extending generally perpendicular first leg 32a toward rear wall 22. Second leg 32b is generally parallel with walls 24, 26. The container 14 is preferably made from a durable, transparent, shatter-resistant plastic such as polycarbonate, which protects the system 10 and allows a user to view fingerprint bearing objects within the container.

Figure 2:
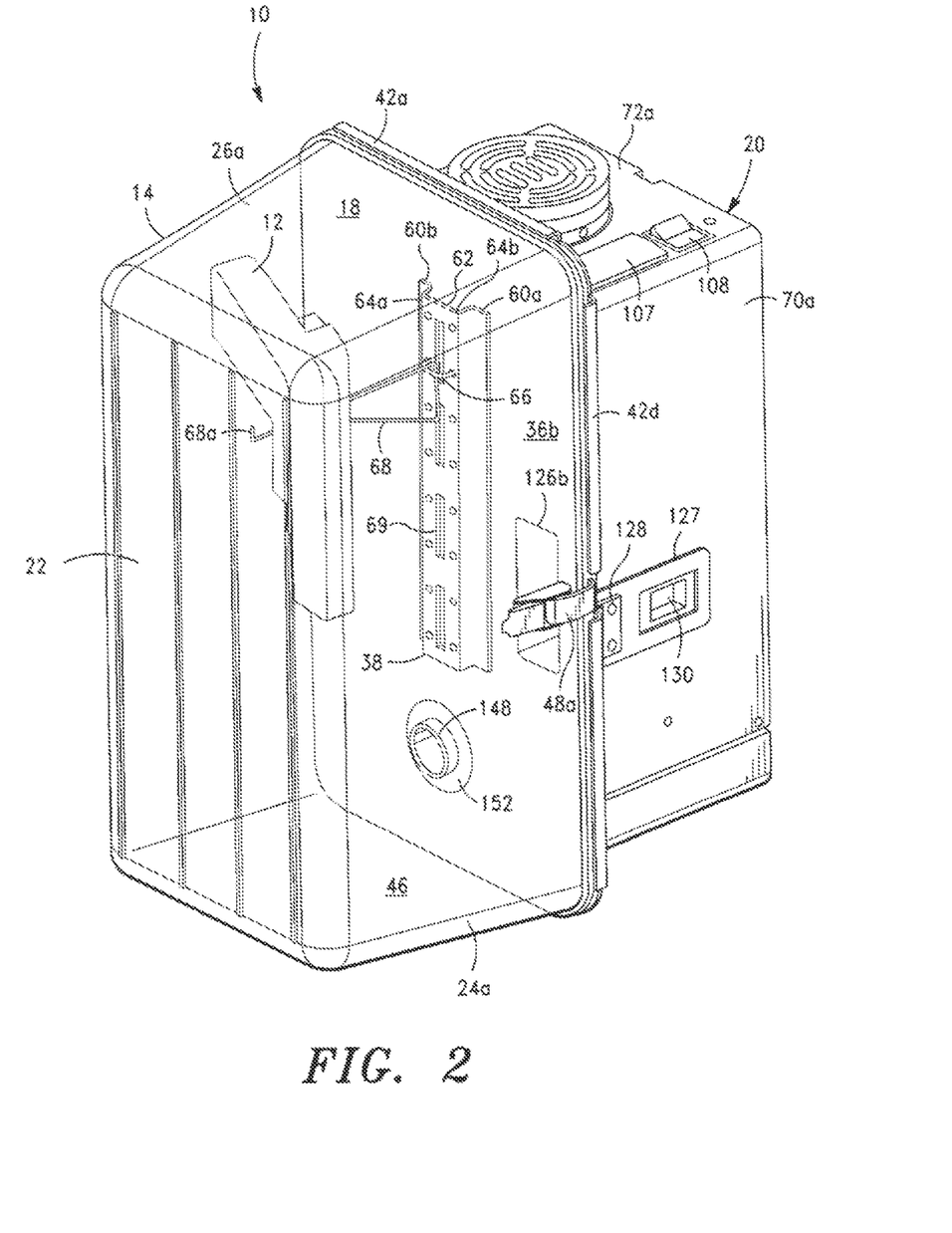
FIG. 2 is a perspective view of the system of FIG. 1.
Figure 3:
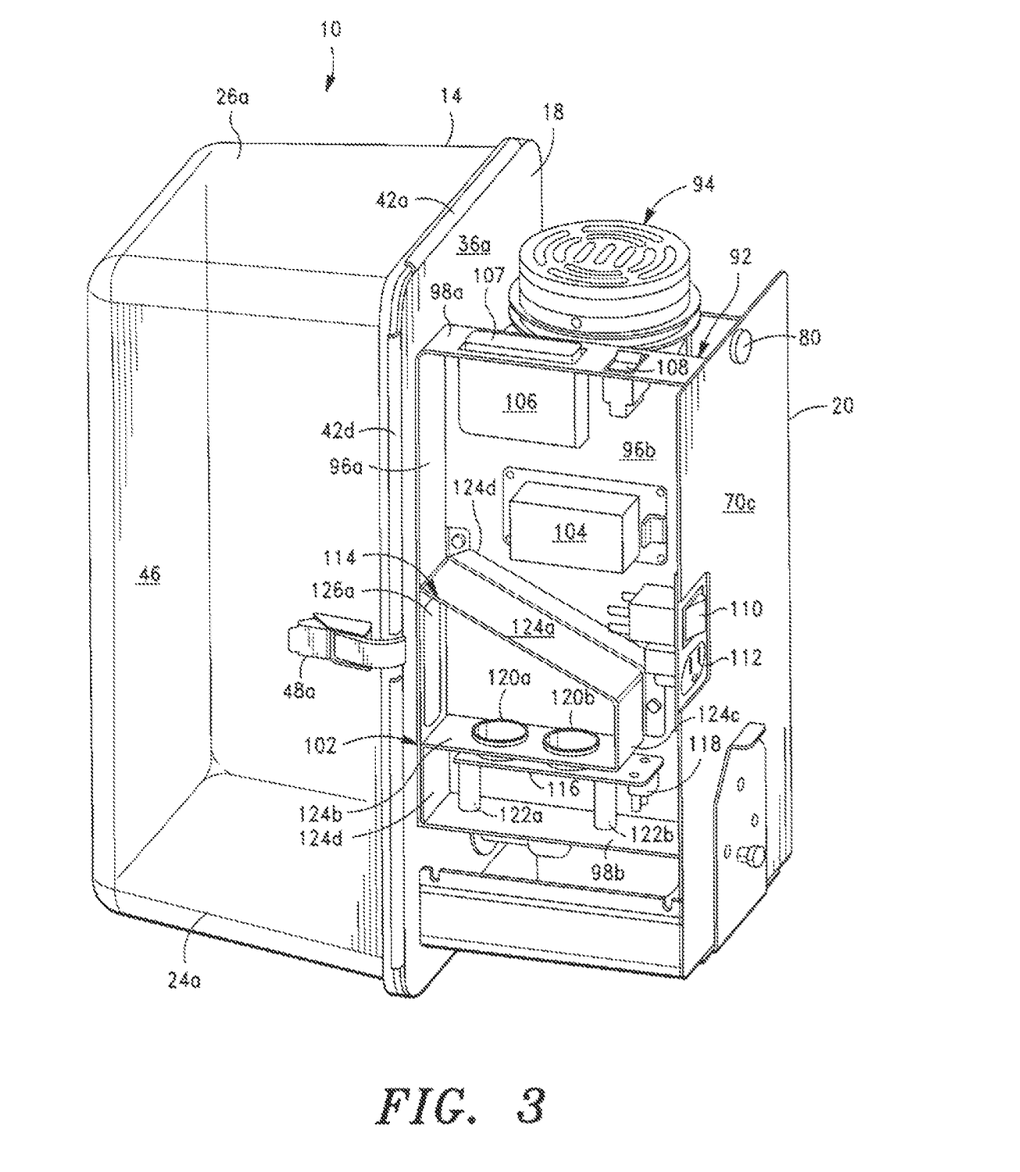
FIG. 3 is a perspective view of the system of FIG. 1 with a housing side wall removed.
Figure 4:
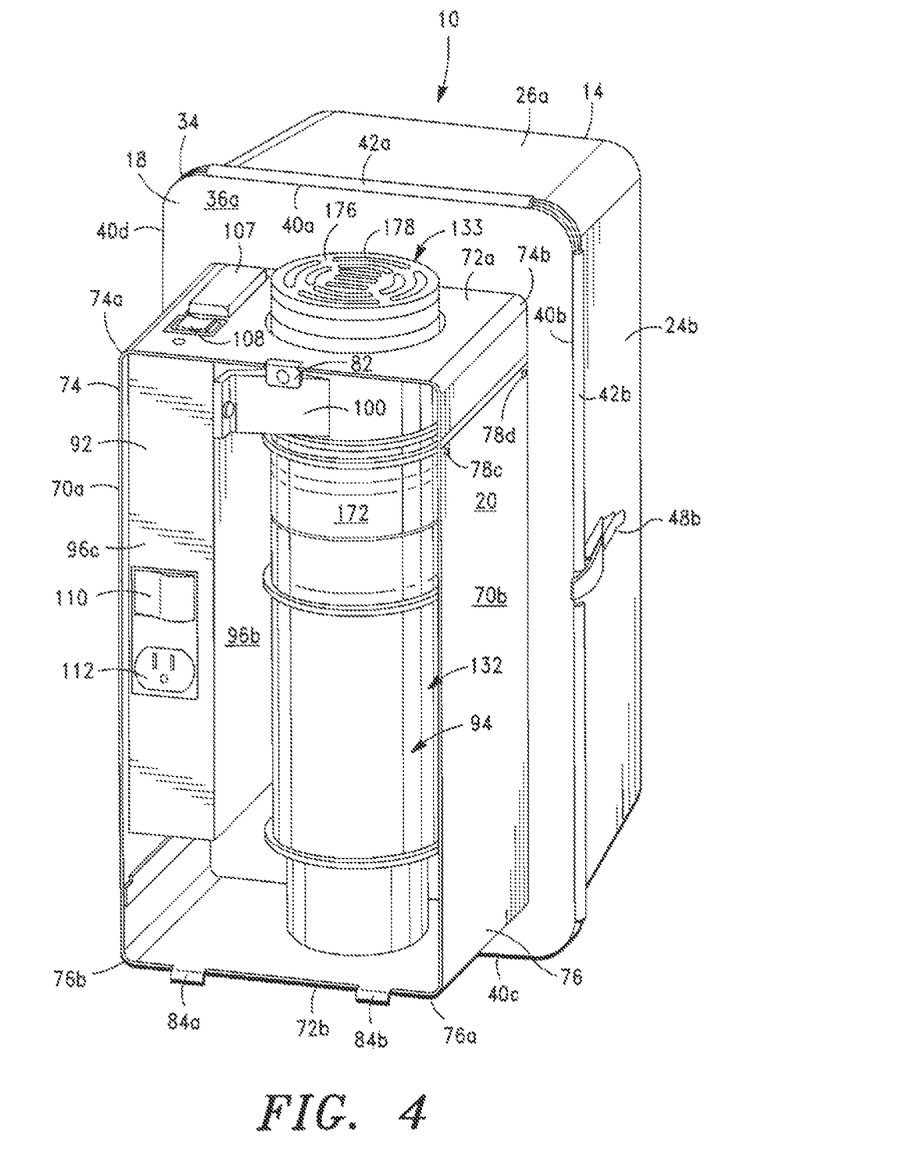
FIG. 4 is a perspective view of the system of FIG. 1 with a housing side wall removed.
Figure 5:
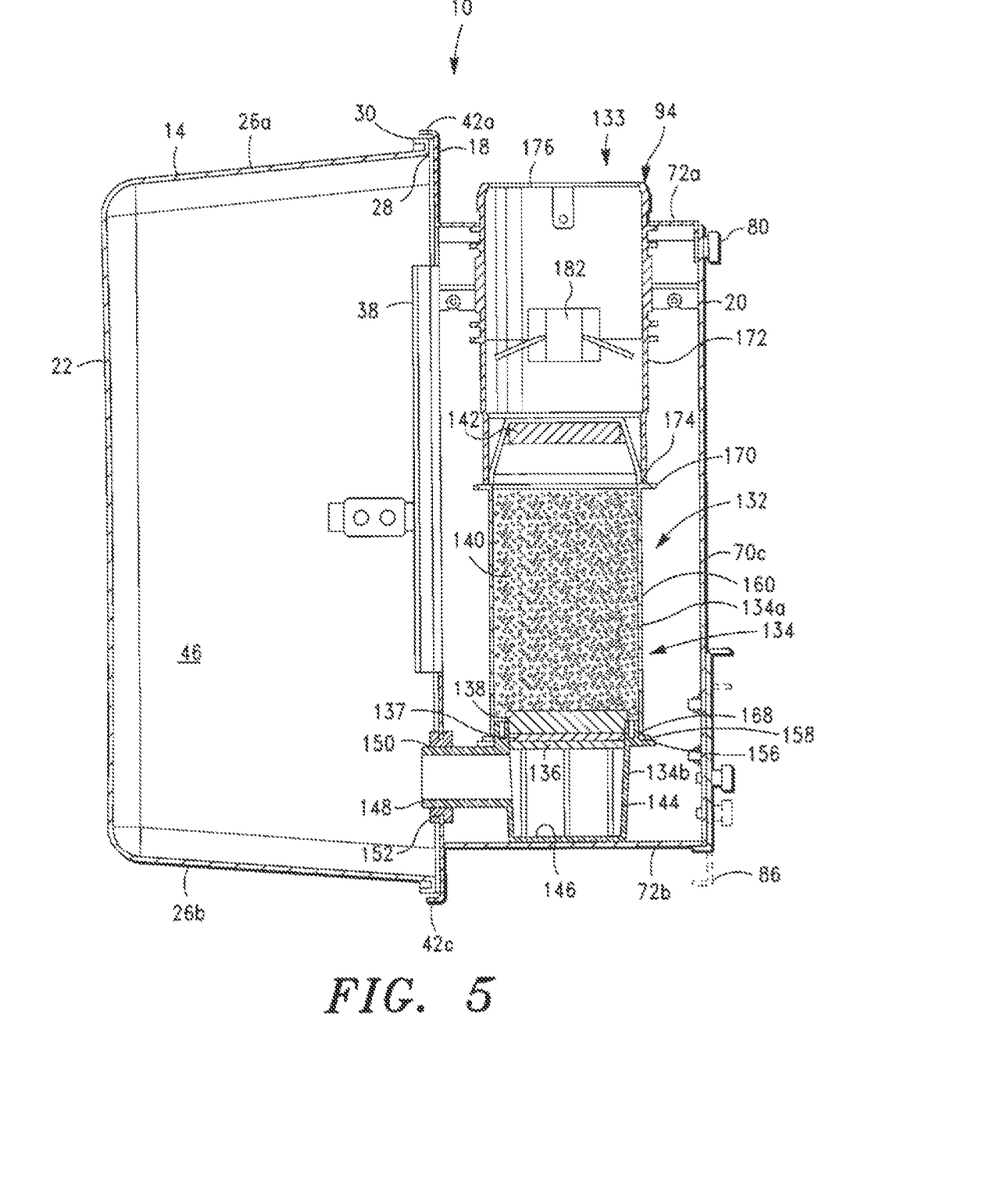
FIG. 5 is a cross-sectional view through the exhaust system of the system of FIG. 1.

Base plate 18 is a generally rectangular sheet of material, preferably stainless steel, having rounded corners, one of which is shown as 34 in FIG. 4, and opposed, generally planar first and second surfaces 36a (FIG. 1) and 36b (FIG. 2). Housing 20 is mounted to first surface 36a, and mounting bracket 38 is mounted to second surface 36b. Referring to FIG. 4, base plate 18 has a peripheral edge consisting of four side edges 40a, 40b, 40c, and 40d joined together at rounded corners 34. Lips 42a, 42b, 42c, and 42d (FIGS. 1-5) extend outwardly from a portion of each of side edges 40a-40d toward second surface 36b. Gaps are presented between lips 42 at the rounded corners of base plate 18. Gaps are also present in lips 42b and 42d to provide clearance for latches 48a and 48b, which are described below. Referring to FIG. 7, lips 42 extend from side edges 40 away from first surface 36a in a direction that is generally perpendicular to first and second surfaces 36a and 36b.

When the system is in its operation position as shown in FIG. 7, portions of rim 30 are received in abutting engagement within lips 42 such that lips 42 are positioned over and generally parallel to corresponding portions of leg 32b of rim 30. Base plate 18 is sized to receive rim with the outer surface of leg 32a positioned facing second surface 36b adjacent side edges 40. A seal 44 is mounted to second surface 36b adjacent side edges 40 and is preferably sized such that it is in abutting engagement with first leg 32a. In this manner, seal 44 provides an airtight seal between base plate 18 and the interior of container 14 when the system is in its operation position for preventing fumes from escaping the container 14 during fingerprint development.

Figure 8:
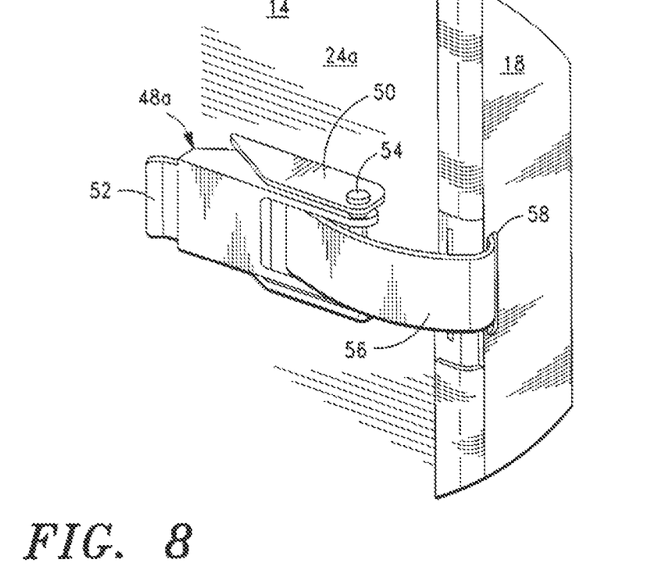
FIG. 8 is close-up view of a latch engaging the base plate.
Figure 9:
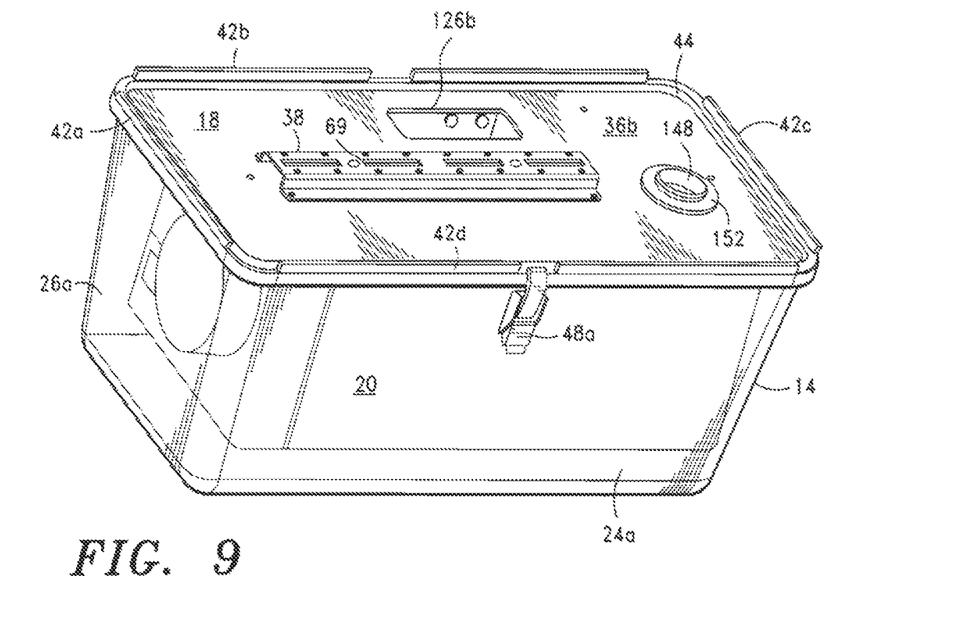
FIG. 9 is a perspective view of the system in the transport position.
Figure 10:
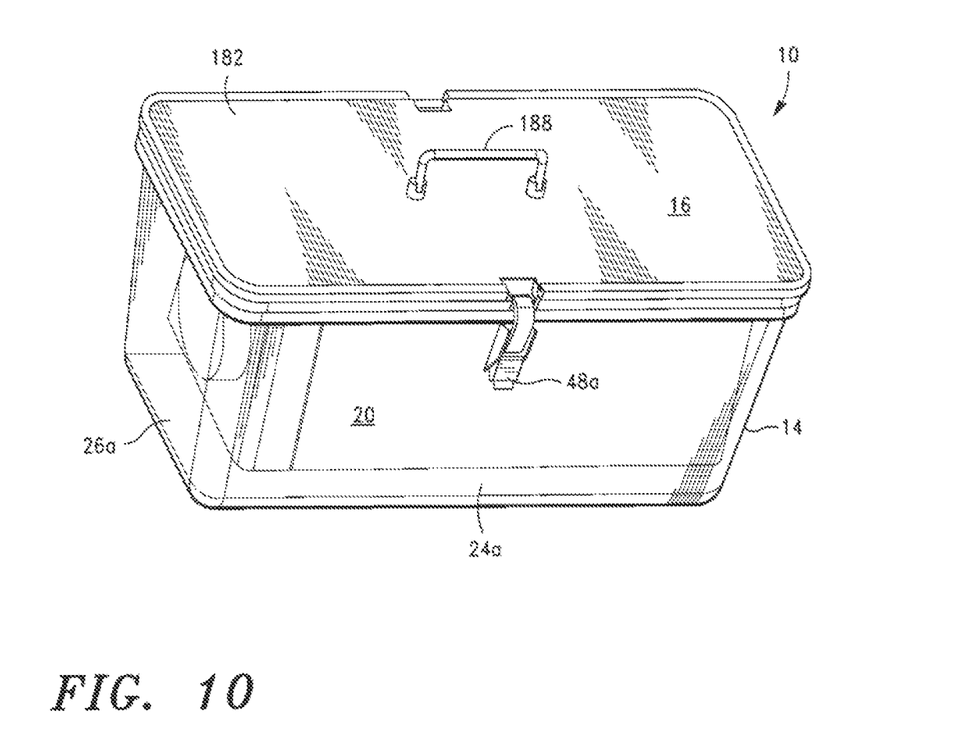
FIG. 10 is a perspective view of the system with a cover in the transport position.

Base plate 18 is moveable between the operation position shown in FIGS. 1-5 and 7-8 and the transport position shown in FIGS. 9-12. In the operation position, second surface 36b of base plate 18 is positioned adjacent or facing rim 30 of container 14 to substantially enclose an interior volume 46 (FIG. 2) that is defined by the plurality of joined walls 22, 24, 26 and base plate 18. In the transport position, first surface 36a of base plate 18 is positioned adjacent or facing rim 30 of the container 14 and the housing 20 is positioned within the container 14, as shown in FIG. 9.

Referring to FIGS. 1, 4, and 8, latches 48a and 48b are mounted to side walls 24a and 24b, respectively, adjacent rim 30. The latches 48a and 48b are operable to secure base plate 18 to container 14 and apply pressure to seal 44. Each latch 48a and 48b is substantially similar: thus, the following description of latch 48a applies to latch 48b. Referring to FIG. 8, latch 48a has a mount 50 that is mounted to side wall 24a, a release 52 that rotates with respect to mount 50 via a pin 54, and a hook 56 that is coupled with release 52. FIG. 8 shows hook 56 in a latched position in which it is received by a slot 58 in base plate 18. When release 52 is rotated away from side wall 24a, hook 56 raises away from base plate 18 and disengages slot 58 as it moves to an unlatched position. Rotating release 52 back toward side wall 24a moves hook 56 downward so that it can engage slot 58 and move back to its latched position. In the latched position, latches 48a and 48b secure base plate 18 to container 14 so that seal 44 can provide an airtight seal between the base plate 18 and the rim 30 of container 14.

Referring to FIG. 2, mounting bracket 38 is provided for holding evidence or other objects on which latent fingerprints will be developed. Mounting bracket 38 comprises two v-shaped legs 60a and 60b that are mounted to second surface 36b of base plate 18, and a perforated surface 62 positioned between legs 60. Perforated surface 62 is joined with legs 60 so that surface 62 is spaced a distance from surface 36b. Surface 62 includes two spaced apart columns of holes 64a and 64b. A u-shaped wire 66 has two ends one of which is received by a hole in column 64a, the other of which is received by an adjacent hole in column 64b. The U-shaped wire 66 is joined with a triangular bracket 68 that extends outward from mounting bracket 38 into the interior of container 14. The triangular bracket 68 suspends handgun 12 within the interior volume 46 of the container 14 so that latent fingerprints may be developed on the handgun. Bracket 68 also comprises an upturned hook 68a so that gun 12 does not inadvertently fall from bracket 68. Perforated surface 62 also has four rectangular slots 69 positioned between columns 64a and 64b. Slots 69 are each operable to receive a microscope slide having a control fingerprint placed thereon. The mounting structure comprising bracket 38, wire 66, and bracket 68 shown in FIG. 2 is illustrative only, and it should be understood that other mounting structures are within the scope of the present invention for suspending any type of object within container 14.

Referring to FIGS. 1-4, housing 20 has side walls 70a, 70b, and 70c and end walls 72a and 72b. Side walls 70a and 70b and end walls 72a and 72b are formed from two sheets of material 74 and 76 (FIG. 4), while side wall 70c is formed from a single sheet of material. Sheet 74 forms end wall 72a and a portion of side walls 70a and 70b, while sheet 76 forms end wall 72b and a portion of side walls 70a and 70b. There are two right angle bends 74a and 74b in sheet 74 forming two corners of the housing. Bend 74a is positioned between side wall 70a and end wall 72a, and bend 74b is positioned between end wall 72a and side wall 70b. Likewise, there are two right angle bends 76a and 76b in sheet 76 forming the other two corners of the housing. Bend 76a is positioned between side wall 70b and end wall 72b, and bend 76b is positioned between end wall 72b and side wall 70a. A portion of sheet 76 forming side wall 70a is overlapped by a portion of sheet 74 and fasteners 78a and 78b (FIG. 1) join the sheets 74 and 76 together. Likewise, a portion of sheet 74 forming side wall 70b is overlapped by a portion of sheet 76 and fasteners 78c and 78d (FIG. 4) join the sheets together. Both of sheets 74 and 76 are secured to base plate 18 in any manner known in the art. Preferably, both of sheets 74 and 76 include tabs (not shown) that extend from walls 70 and 72 over base plate 18, and most preferably, the tabs are secured to base plate 18 with fasteners (not shown).

Referring to FIGS. 3 and 4, side wall 70c is coupled with sheet 74 by a threaded knob 80 that extends through an opening in side wall 70c into a threaded opening in a tab 82 extending from end wall 72a. Side wall 70c is also coupled with sheet 76 via a pair of tabs (not shown) that extend outwardly from the edge of side wall 70c for reception by slots formed in tabs 84a and 84b extending out from end wall 72b. Side wall 70c may be easily removed from the housing 20 for accessing the components positioned within the interior of the housing 20. To remove side wall 70c, knob 80 is first turned or rotated to remove it from threaded engagement with the opening in tab 82. Then, side wall 70c is slid upward until the tabs on the bottom of the side wall are no longer received by the slots in tabs 84a and 84b on end wall 72b.

Referring to FIG. 1, a support 86 is coupled to side wall 70c for stabilizing the housing 20 and container 14 when system 10 is in its operation position. Support 86 is slidable between a first position, shown in solid lines in FIG. 1, and a second position, shown in dashed lines in FIG. 1. In its first position, the support 86 is retracted so that the housing 20 can fit within the interior of container 14 when the system 10 is in its transport position as shown in FIGS. 9 and 10. In its second position, support 86 stabilizes the housing 20 and container 14 when system 10 is in its operation position. Support 86 comprises a first section 86a that is parallel with side wall 70c, a second section 86b that extends perpendicularly outward from section 86a and side wall 70c to form a handle, and a third section 86c that extends perpendicular inward from section 86a to form a foot that abuts the outer surface of end wall 72b when support 86 is in its first, retracted position and that contacts a supporting surface in its second position.

Support 86 is maintained in its first position and its second position by a spring loaded knob 88. Knob 88 extends through an opening in support 86 into one of two openings (not shown) formed in side wall 70c. Knob 88 is received by the first opening in side wall 70c when support 86 is in its first position, and the knob 88 is received by the second opening in side wall 70c when support 86 is in its second position. Support 86 is also mounted to side wall 70c with three fasteners 90a, 90b, and 90c, which extend through openings in support 86 into slots (not shown) formed in side wall 70c. The slots that receive fasteners 90a-90c are sized such that the fasteners 90a-90c can slide the length of the slots as the support 86 moves between its first and second positions. The fasteners 90a, 90b, and 90c prevent support 86 from rotating with respect to side wall 70c.

Referring to FIGS. 3 and 4, housing 20 encloses and protects a second housing 92 and an exhaust system 94. Second housing 92 is formed from side walls 96a, 96b, and 96c that are joined with end walls 98a and 98b, respectively. Side wall 96a is mounted to base plate 18 and may also be mounted to side wall 70a of housing 20. Further, there is a bracket 100 that couples side wall 96b and exhaust system 94 (FIG. 4). The interior of the second housing 92 may be enclosed by a fourth side wall that is joined to walls 96 and 98, and/or by side wall 70a of housing 20.

Referring to FIG. 3, second housing 92 mounts a heater system 102, a transformer 104 for the exhaust system 94, a controller 106 having a display 107, a switch 108, a circuit breaker 110, and a power cord receptacle 112.

The heater system 102 includes a heater compartment 114, a heater 116, a thermostat 118, two wells 120a and 120b formed in the heater compartment 114 for receiving a material to be heated, and two columns 122a and 122b separating heater 116 from wall 98b.

Heater compartment 114 includes top and bottom walls 124a and 124b that are joined with a side wall 124c. There is a flange 124d extending from the walls 124a-c for mounting the heater compartment 114 on walls 96a and 96b. The walls 124a-c of the heater compartment 114 partially enclose a volume that is in fluid communication with the interior volume 46 of container 14 via aligned openings 126a in wall 96a and 126b in base plate 18 (FIG. 2) when the system 10 is in its operation position. Top wall 124a is angled upwardly toward wall 96a such that the area of compartment 114 is larger adjacent the openings 126. In an alternative embodiment, top wall 124a may be parallel with wall 124b. Side wall 70a, or a fourth side wall of housing 92 that is joined to walls 96a, 96c, and 98a-b, along with walls 124a-c enclose and seal the heater compartment 114 to prevent fumes from escaping the compartment. Preferably, a high temperature sealant is applied to the seams between the walls 124a-c and flange 124d of heater compartment 114 and walls 70a, 96a, and 96b to prevent fumes from escaping the compartment.

Referring to FIGS. 1 and 2, door 127 is mounted to side wall 70a of housing 20 with a hinge 128 for accessing heater compartment 114 via an opening in side wall 70a. Door 127 has a closing mechanism 130, which is slidable between a locked position in which it engages a portion of side wall 70a for preventing door 127 from opening and an open position in which door 127 may be opened. This door may include an optional gasket (not shown) along the interior periphery of the door to seal the door when closed.

There are two openings in bottom wall 124b of heater compartment 114 for receiving wells 120a and 120b, which are preferably removable foil pans. Alternatively, the wells 120a and 120b may be formed directly into wall 124b. One of the wells 120a and 120b preferably receives a fingerprint development material such as cyanoacrylate and the other of wells 120a and 120b preferably receives water. The wells 120a and 120b extend through the openings in bottom wall 124b to a position where they are adjacent heater 116. Wells 120a and 120b may abut heater 116 or there may be a gap between the wells 120a and 120b and heater 116. Heater 116 is operable to vaporize the cyanoacrylate and water within wells 120a and 120b to develop latent fingerprints on an object within container 14, as discussed in full below. Wells 120a and 120b are preferably about ¼ to ¾ inches deep and 1 to 1.5 inches in diameter. Most preferably, the wells 120a and 120b are approximately 5/16 inches deep and 1.2 inches in diameter. Columns 122a and 122b separate heater 116 from bottom wall 98b of housing 92 for insulating the housing 92.

Controller 106 is mounted to wall 96b and display 107 on controller 106 extends through an opening in wall 98a and an opening in wall 72a (FIG. 1). Display 107 is operable to display the actual temperature of heater 116 and a desired or set temperature of the heater 116. Controller 106 preferably includes one or more user input devices that allow an operator of the system 10 to set a preferable temperature for heater 116, which is displayed on display 107. Controller 106 is electrically coupled with receptacle 112 for providing power to the controller 106 and display 107. Controller 106 is also electrically coupled with heater 116 so that it may regulate the supply of power to heater 116 for maintaining the heater 116 at the desired or set temperature. Controller 106 is coupled to a metal plate (not shown) on the top surface of the heater 116 with a thermocouple to regulate the heater's temperature. Controller 106 is preferably programmed to limit the minimum and maximum temperature set points of heater 116 within a range of safe and effective operation. Preferably, the minimum temperature set point is between approximately 120 to 150 degrees Fahrenheit, and the maximum temperature set point is between approximately 320 to 350 degrees Fahrenheit. Further, thermostat 118 is electrically coupled in series with controller 106 and heater 116 in order to limit the maximum temperature of the heater 116 in the event that controller 106 fails. Controller 106 is preferably a solid state electronic device. Display 107 is preferably an LCD display; although, it is within the scope of the invention for display 107 to be any type of display. It is also anticipated that the controller and display may incorporate a timer and time display respectively for setting, a fixed period of operation of the heater.

Switch 108 is mounted to wall 98a and extends through an opening in wall 98a and wall 72a (FIG. 1). Switch 108 is electrically coupled to heater 116, the exhaust system 94 via transformer 104, and power cord receptacle 112 for selectively providing electrical current to the heater 116 and a fan within the exhaust system 94, which is described below. Preferably, switch 108 is a three way switch having an off position, a heat position, in which the heater 116 is electrically coupled with power cord receptacle 112 subject to instructions from controller 106, and a vent position, in which a fan within the exhaust system 94 is electrically coupled with receptacle 112 via transformer 104.

Circuit breaker 110 and power cord receptacle 112 are mounted to wall 96c and extend through openings in wall 96c and wall 70c (FIG. 1). Circuit breaker 110 is electrically coupled with receptacle 112 and comprises a switch that is moveable between an on position, in which electrical current may flow from the receptacle 112 to the components of system 10, and an off position, blocking current flow from the receptacle 112 to the components of system 10. Power cord receptacle 112 is a conventional electrical receptacle that is operable to engage an electrical plug that is coupled with a permanent source of electric alternating current for powering the system 10. The wires that electrically couple exhaust system 94, transformer 104, controller 106, switch 108, circuit breaker 110, receptacle 112, heater 116, and thermostat 118 are not shown in the drawings for clarity.

Figure 6:
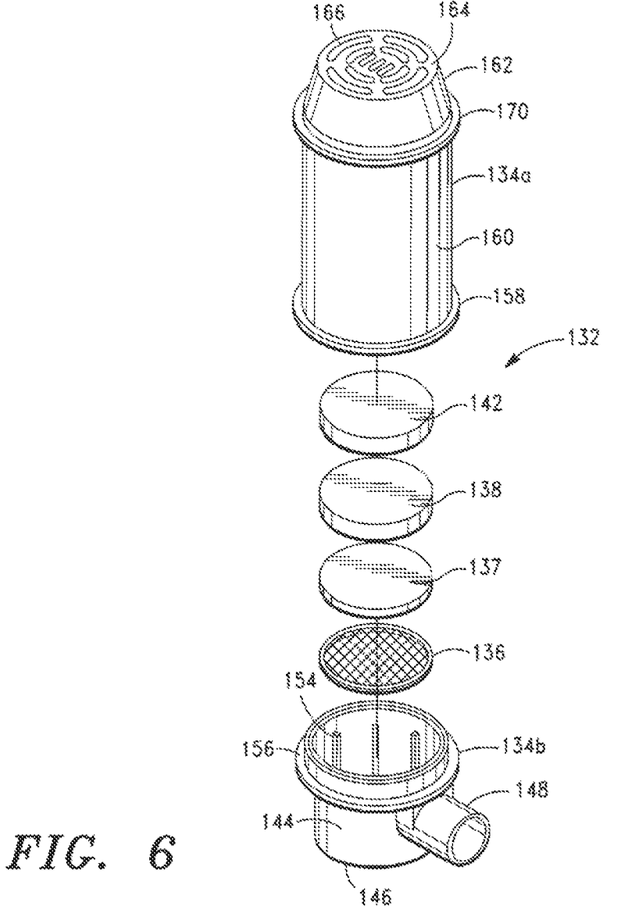
FIG. 6 is an exploded view of a portion of the exhaust system.

Referring to FIGS. 4-6, exhaust system 94 comprises a filter section 132 in fluid communication with the interior 46 of container 14 and a fan section 133 in fluid communication with filter section 132. Referring to FIG. 5, filter section 132 includes housing 134 comprising top section 134a, bottom section 134b, screen 136, particulate filter 137, foam disk 138, activated carbon granules 140, and foam disk 142 positioned within housing 134. Particulate filter 137 is operable to clean air passing from container 14 through the filter 137 by filtering droplets of cyanoacrylate within the air. Activated carbon granules 140 are operable to adsorb vaporous cyanoacrylate and odors within air passing from container 14 through the granules 140.

Bottom section 134b includes a cylindrical side wall 144 joined with a bottom wall 146 and a cylindrical inlet 148 extending perpendicularly outward from side wall 144. Inlet 148 is in fluid communication with a volume enclosed by side wall 144 and bottom wall 146. Referring to FIG. 5, inlet 148 extends through an opening 150 in base plate 18 into the interior 46 of container 14. There is a mounting seal 152 positioned within opening 150 that encircles inlet 148 for preventing fumes from escaping container 14. A plurality of ribs 154 (FIG. 6) are formed in or mounted on an interior surface of side wall 144 for supporting screen 136, which supports particulate filter 137 and foam disk 138. Screen 136 is preferably made from metal. Particulate filter 137 preferably comprises a polyester pre-filter media. Filter 137 may however comprise other types of filters. Foam disk 138 contains the activated carbon granules 140 to prevent them from passing through particulate filter 137 and screen 136. Flange 156 extends outward from side wall 144 for mating with flange 158 on upper section 134a of housing 134.

Referring to FIG. 6, upper section 134a includes a cylindrical side wall 160, flange 158 that extends outward from the side wall 160, a truncated cone section 162 extending upward from side wall 160, and a top plate 164 joined to the top of section 162. A plurality of openings 166 are formed in top plate 164 for allowing gas to flow from filter section 132 to fan section 133. Referring to FIG. 5, side wall 160 defines an opening 168 that receives the portion of side wall 144 of bottom section 134b above flange 156. There may be a slight interference fit between the opening 168 and side wall 144 so that upper and bottom sections 134a and 134b are not inadvertently separated. Foam disk 142 is pressed within the interior of cone section 162 adjacent top plate 164 for preventing the activated carbon granules 140 from spilling out of openings 166 when system 10 is transported. Flange 170 extends outward from side wall 160 adjacent cone section 162 for abutting fan section 133. The activated carbon granules 140 are operable to remove organic chemicals and odors out of gas flowing through housing 134.

Referring to FIGS. 4 and 5, fan section 133 comprises a cylindrical side wall 172 with an opening 174 that receives the truncated cone section 162 of housing 134, and a top plate 176 joined to side wall 172. A plurality of outlet openings 178 are formed in top plate 176 for allowing gas to flow from the fan section 133 into the atmosphere or into an optional exhaust duct 180, shown in FIG. 1. A fan 182 is positioned within a volume defined by side wall 172. The fan 182 is driven by a motor (not shown) that is electrically coupled with transformer 104 for receiving electrical current from receptacle 112 as discussed above. When powered on, fan 182 is operable to draw air, other gases, and/or particulate matter from the interior of container 14 through a conduit defined by inlet 148, housing 134, and side wall 172. The fan 182 discharges the air, other gases, and/or particulate matter through the openings 178 into the atmosphere or optional exhaust duct 180. The exhaust duct 180 may be of any length necessary to discharge the air, other gases, and/or particulate matter to a desired location such as outside of a building or vehicle. The exhaust duct 180 is preferably collapsible to facilitate transport. Housing 134 and side wall 172 are preferably molded plastic, although it is within the scope of the invention for them to be formed from any material.

Figure 11:
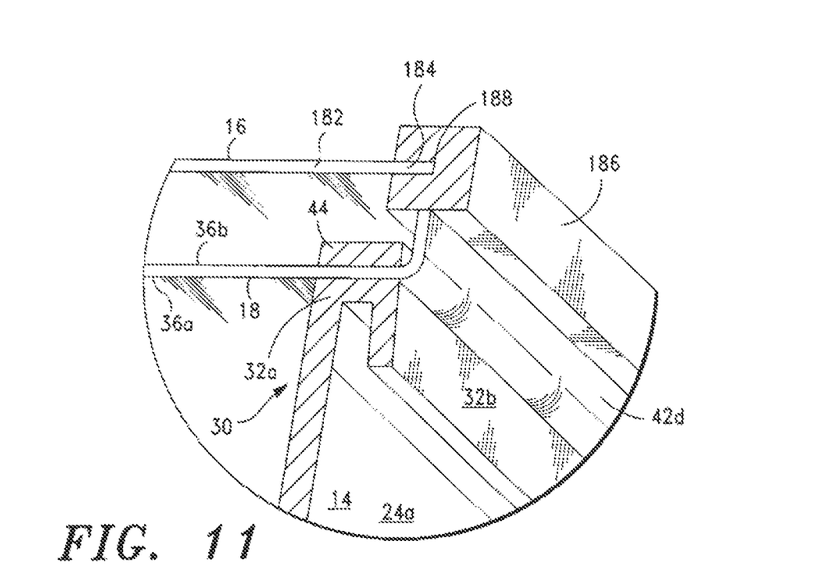
FIG. 11 is a close-up view of sealing edges of the base plate, cover, and container in the transport position.

Referring now to FIG. 8, when it is desired to transport system 10, system 10 is converted from its operation position to its transport position by raising release 52 on each of latches 48a and 48b to remove hook 56 from slot 58. Then, base plate 18 and housing 20 are flipped over to the position shown in FIG. 9 in which housing 20 is positioned within the interior 46 of container 14. In this position, the first surface 36a of base plate 18 abuts the first leg 32a of rim 30, as shown in detail in FIG. 11, so that the rim 30 supports the base plate 18. A cover 16, shown in FIGS. 10 and 11, is placed on top of base plate 18 adjacent second surface 36b for protection and to facilitate transport.

Cover 16 includes a flat plate 182 having a peripheral edge 184 that mounts a seal 186. Seal 186 is rectangular with an opening 188 that receives the peripheral edge 184 of plate 182. Seal 186 abuts the lips 42a-d of base plate 18 when cover 16 is positioned on top of the base plate 18. Referring to FIG. 10, a handle 188 is mounted in the center of plate 182 to facilitate transporting system 10.

Figure 12:
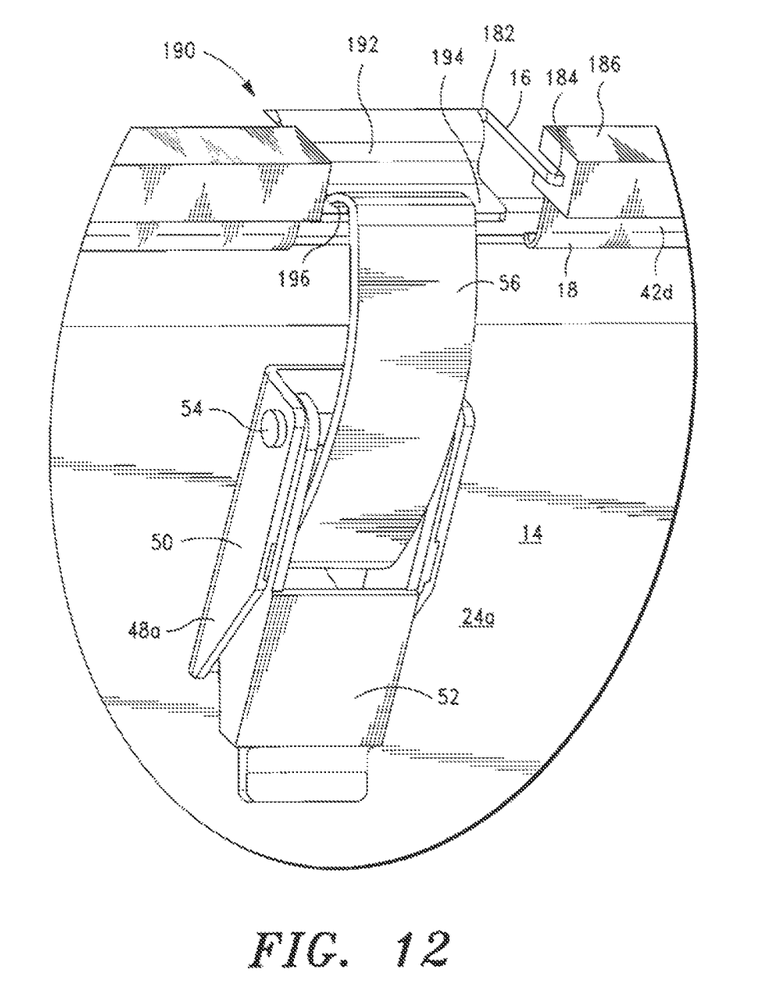
FIG. 12 is a close-up view of the latch engaging the cover in the transport position.

Referring to FIG. 12, cover 16 is secured to container 14 with latch 48a. A latch engaging structure 190 is formed into the peripheral edge 184 of plate 182. The latch engaging structure 190 includes a first section 192 extending downward from plate 182 and a second section 194 extending outward from section 192. A slot 196 is formed into section 194 for receiving the hook 56 of latch 48a in a similar manner as described above with respect to slot 58 of base plate 18. Cover 16 also has structure that engages latch 48b in a similar manner as shown in FIG. 12.

In operation, system 10 is transported from storage to a crime scene, mobile or permanent laboratory, or other location in its transport position, which is shown in FIG. 10. The system 10 has a weight and size that permits it to be carried by a single person via handle 188. Upon reaching its destination, system 10 is converted into its operation position, which is shown in FIG. 1. To convert system 10 into its operation position, latch release 52 on each of latches 48a and 48b is first rotated outward from container 14 to raise hook 56 so that it disengages slot 196 on cover 16 (FIG. 12). Cover 16 is then removed from the container 14 so that the system 10 appears as in FIG. 9. Next, base plate 18 is lifted in order to remove housing 20 from the interior 46 of container 14. Container 14 is then positioned on its side to rest on wall 26b and base plate 18 is flipped up such that housing 20 is positioned facing away from container 14. Before the second surface 36b of base plate 18 is positioned adjacent rim 30 of the container 14, wire 66 (FIG. 2) is inserted into an appropriate set of holes 64a and 64b in mounting bracket 38, and an object containing undeveloped fingerprints, such as gun 12, is suspended from bracket 68. A control glass slide, on which the operator has placed his/her own latent fingerprint, may also be placed partially within one of slots 69 on mounting bracket 38 to provide a visible cue to the operator that the fingerprint has developed properly.

The second surface 36b of base plate 18 is then positioned so that it abuts the rim 30 of container 14 in the position shown in FIGS. 1-5 and 7. Referring to FIG. 8, the hook 56 on each of latches 48a and 48b is positioned adjacent to the slot 58 in base plate 18 and the release 52 is rotated toward container 14 so that the hook 56 engages slot 58. When the hook 56 on each of latches 48a and 48b engages the slots 58 on the base plate 18, the container 14 is sealed to the base plate 18 so that cyanoacrylate fumes within the container 14 cannot escape. To stabilize housing 20 and container 14 when they are in the position shown in FIGS. 1-5, support 86 is moved from its first position to its second position, shown in dashed lines in FIGS. 1 and 5.

With the container 14 and housing 20 in the position shown in FIG. 2, door 127 is opened and wells 120a and 120b are removed from heater compartment 114 so that water and cyanoacrylate can be placed in them (FIG. 3). Preferably, the cyanoacrylate is added drop by drop until it covers the bottom of one of wells 120a and 120b to ensure that the concentration of cyanoacrylate within container 14 is sufficient to develop latent fingerprints without completely covering or overdeveloping the prints. Switch 108 is switched to its heat position so that heater 116 begins heating up. The operator preferably adjusts the desired or set temperature of heater 116 using controller 106. The controller 106 displays on display 107 the actual temperature of heater 116 and the desired or set temperature of the heater 116. The controller 106 energizes the heater 116 as needed to maintain the temperature at the desired level. When the heater 116 reaches the set temperature, the removable well 120a or 120b containing water is placed back into heater compartment 114 to increase the relative humidity within the container 14 to a desired level. Door 127 is then shut to seal heater compartment 114 so that water vapor cannot escape the compartment.

As the heater 116 vaporizes the water within one of wells 120a and 120b, the water vapor moves from heater compartment 114 through openings 126a and 126b into container 14. Preferably, the relative humidity within container 14 is increased to approximately 80% because it is believed that optimum fingerprint development occurs at approximately this level of humidity. A hygrometer (not shown) may be positioned within container 14 where it is visible through the container's walls for determining the relative humidity within container 14. Optionally, the hygrometer may be connected to controller 106 for displaying the relative humidity on display 107. Once the relative humidity reaches the desired level, the well 120a or 120b containing water may be removed from compartment 114, or it may be left within compartment 114 for maintaining the relative humidity at approximately the desired level.

Once the relative humidity within container 14 reaches the desired level, door 127 is opened and the well 120a or 120b containing cyanoacrylate is placed within heater compartment 114. Door 127 is then closed so that cyanoacrylate fumes do not escape the heater compartment 114. The heater 116 vaporizes the cyanoacrylate, and the cyanoacrylate fumes move from heater compartment 114 through openings 126a and 126b into container 14. The cyanoacrylate fumes form a white polymer on the ridges of any latent fingerprints on the objects suspended within container 14 to preserve and make them visible. The foremost advantage of system 10 is its ability to preserve fingerprints at a crime scene thereby reducing the risk that the prints will be smeared or rubbed off during handling and transport of the evidence. While the cyanoacrylate is vaporizing or fuming out of one of wells 120a and 120b, the operator preferably observes the control fingerprint placed on the slide within one of slots 69 to monitor the reaction of the cyanoacrylate with the print. When the operator decides that the print has been properly developed, switch 108 is moved from its heat position to its vent position.

When switch 108 is moved to its vent position, heater 116 and controller 106 are turned off and fan 182 within exhaust system 94 is powered on. The fan 182 draws the air and cyanoacrylate fumes from container 14 to prevent overdeveloping the fingerprints on the objects within the container 14. Preferably, after switch 108 is moved to the vent position, door 127 is opened slightly to allow fresh air to enter the heater compartment 114 and container 14 to assist in directing the cyanoacrylate fumes into the exhaust system 94. The air and cyanoacrylate fumes move from container 14 through inlet 148 and into housing 134 of exhaust system 94. In housing 134, the air and cyanoacrylate fumes pass through particulate filter 137 which removes droplets of cyanoacrylate from the air. Then, the air and cyanoacrylate fumes pass through activated carbon granules 140, which adsorb vaporous cyanoacrylate within the air and remove odors from the air. The filtered air then exits housing 134, passes through fan section 133, and either enters the atmosphere surrounding system 10 or passes through the optional exhaust duct 180, which guides the filtered air to a desired location.

With the cyanoacrylate fumes exhausted from container 14, the objects within container 14, such as gun 12, are retrieved by releasing the base plate 18 from container 14 with latches 48a and 48b as described above. The above described process can be repeated with additional evidence that needs to be processed for prints, or the system 10 can be converted into its transport position so that it may be transported to storage.

From the foregoing it will be seen that this invention is one well adapted to attain all ends and objectives herein-above set forth, together with the other advantages which are obvious and which are inherent to the invention.

Since many possible embodiments may be made of the invention without departing from the scope thereof, it is to be understood that all matters herein set forth or shown in the accompanying drawings are to be interpreted as illustrative, and not in a limiting sense.

While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

What is claimed and desired to be secured by Letters Patent is as follows:

1. A fingerprint development system, comprising:
a container having a plurality of joined walls that present an opening; and
a base plate having opposed first and second surfaces, said first surface mounting a heater that is operable to heat a fingerprint development material, said base plate moveable between a transport position, in which said first surface is adjacent said opening and said heater is positioned within said container, and an operation position, in which said second surface is adjacent said opening to substantially enclose an interior volume that is defined by said plurality of joined walls and said base plate.

2. The system of claim 1, further comprising an exhaust system mounted to said first surface of said base plate, said exhaust system comprising a conduit that is in fluid communication with said interior volume when said base plate is in its operation position via an exhaust opening in said base plate.

3. The system of claim 2, further comprising a filter positioned within said conduit of said exhaust system.

4. The system of claim 2, further comprising a first filter positioned within said conduit of said exhaust system adjacent to said exhaust opening, and a carbon filter positioned within said conduit adjacent to said first filter.

5. The system of claim 2, wherein said exhaust system comprises an input port that is coupled with said base plate in fluid communication with said exhaust opening, and an outlet port, and further comprising an exhaust duct coupled with said outlet port and in fluid communication with said conduit of said exhaust system.

6. The system of claim 2, wherein said exhaust system comprises a fan positioned within said conduit, said fan configured to evacuate at least a portion of a gas from said interior volume when said base plate is in its operation position.

7. The system of claim 6, further comprising a switch electrically coupled with said heater, said fan, and an electrical power source, said switch moveable between an off position, a heat position, in which said heater is electrically coupled with said electrical power source, and a vent position, in which said fan is electrically coupled with said electrical power source.

8. The system of claim 1, further comprising a temperature controller electrically coupled with said heater, said temperature controller operable to regulate the temperature of said heater.

9. The system of claim 1, further comprising a mounting surface that is mounted to said second surface of said base plate, said mounting surface operable to support a fingerprint bearing material within said interior volume when said base plate is in its operation position.

10. The system of claim 1, further comprising a seal that is positioned adjacent to a peripheral edge of said second surface of said base plate, said seal positioned between said second surface of said base plate and a periphery of said opening in said container when the base plate is in its operation position.

11. The system of claim 1, further comprising a latch mounted to one of said walls of said container, said latch moveable between a latched position, in which it secures said base plate to said container, and an unlatched position.

12. The system of claim 11, further comprising a cover that is positioned adjacent to said second surface of said base plate when said base plate is in its transport position, said latch engaging said cover when in the latched position to secure said cover to said container.

13. The system of claim 1, further comprising a heater compartment mounted on said first surface of said base plate and in fluid communication with said interior volume when said base plate is in its operation position via a heater opening in said base plate, said heater compartment comprising a well that is operable to receive the fingerprint development material and that is positioned adjacent to said heater.

14. The system of claim 13, wherein said heater compartment comprises a second well positioned adjacent to said heater for receiving water.

15. The system of claim 13, further comprising a heater compartment door that is moveable between an open position and a closed position in which it seals said heater compartment.

16. The system of claim 13, wherein said well comprises a foil pan that is operable to receive said fingerprint development material.

17. The system of claim 13, further comprising a housing mounted to said first surface of said base plate, said housing enclosing at least a portion of said heater compartment, said housing comprising a support that is moveable between a first position, for positioning said housing within said container when said base plate is in its transport position, and a second position, in which said support stabilizes said housing and said container when said base plate is in its operation position.

18. A fingerprint development system, comprising:
a container comprising a plurality of joined walls that present an opening and a rim surrounding said opening;
a base plate comprising opposed first and second surfaces, said base plate moveable between a transport position, in which said first surface is abutting said rim of said container, and an operation position, in which said second surface is abutting said rim of said container to substantially enclose an interior volume that is defined by said plurality of joined walls and said base plate;
a heater compartment mounted on said first surface of said base plate and operable to receive a fingerprint development material, said heater compartment in fluid communication with said interior volume when said base plate is in its operation position via a heater opening in said base plate;
a heater mounted on said base plate adjacent to said heater compartment, said heater operable to heat the fingerprint development material; and
an exhaust system mounted on said first surface of said base plate, said exhaust system comprising a conduit that is in fluid communication with said interior volume when said base plate is in its operation position via an exhaust opening in said base plate.

19. The system of claim 18, further comprising a filter positioned within said conduit of said exhaust system.

20. The system of claim 18, further comprising a first filter positioned within said conduit of said exhaust system adjacent to said exhaust opening, and a carbon filter positioned within said conduit adjacent to said first filter.

21. The system of claim 18, wherein said exhaust system comprises an input port that is coupled with said base plate in fluid communication with said exhaust opening, and an outlet port, and further comprising an exhaust duct coupled with said outlet port and in fluid communication with said conduit of said exhaust system.

22. The system of claim 18, wherein said exhaust system comprises a fan positioned within said conduit, said fan configured to evacuate at least a portion of a gas from said interior volume when said base plate is in its operation position.

23. The system of claim 22, further comprising a switch electrically coupled with said heater, said fan, and an electrical power source, said switch moveable between an off position, a heat position, in which said heater is electrically coupled with said electrical power source, and a vent position, in which said fan is electrically coupled with said electrical power source.

24. The system of claim 18, further comprising a mounting surface that is mounted to said second surface of said base plate, said mounting surface operable to support a fingerprint bearing material within said interior volume when said base plate is in its operation position.

25. The system of claim 18, wherein said heater compartment comprises a well that is positioned adjacent to said heater for receiving the fingerprint development material.

26. The system of claim 18, further comprising a housing mounted to said first surface of said base plate, said housing enclosing at least a portion of said heater compartment and said exhaust system, said housing comprising a support that is moveable between a first position, for positioning said housing within said container when said base plate is in its transport position, and a second position, in which said support stabilizes said housing and said container when said base plate is in its operation position.

27. The system of claim 18, further comprising a latch mounted to one of said walls of said container, said latch moveable between a latched position, in which it secures said base plate to said container, and an unlatched position.

28. The system of claim 27, further comprising a cover that is positioned adjacent to said second surface of said base plate when said base plate is in its transport position, said latch engaging said cover when in the latched position to secure said cover to said container.

* * * * *